United States Patent
London

(10) Patent No.: US 9,198,803 B1
(45) Date of Patent: Dec. 1, 2015

(54) DRESSING DEVICE FOR OFFLOADING AND TREATING AN ULCER

(76) Inventor: David S. London, Dallas, TX (US)

( * ) Notice: Subject to any disclaimer, the term of this patent is extended or adjusted under 35 U.S.C. 154(b) by 1069 days.

(21) Appl. No.: 13/245,047

(22) Filed: Sep. 26, 2011

(51) Int. Cl.
*A61F 13/02* (2006.01)

(52) U.S. Cl.
CPC .................................. *A61F 13/0203* (2013.01)

(58) Field of Classification Search
CPC combination set(s) only.
See application file for complete search history.

(56) References Cited

U.S. PATENT DOCUMENTS

| | | | |
|---|---|---|---|
| 5,197,942 A | 3/1993 | Brady | |
| 5,329,705 A | 7/1994 | Grim | |
| 5,628,723 A * | 5/1997 | Grau | 602/53 |
| 5,944,683 A | 8/1999 | Baranowski | |
| 6,071,267 A * | 6/2000 | Zamierowski | 604/289 |
| 6,593,508 B1 * | 7/2003 | Harder | 602/56 |
| 6,610,897 B2 | 8/2003 | Cavanagh et al. | |
| 6,720,470 B2 | 4/2004 | Cavanagh et al. | |
| 7,118,545 B2 | 10/2006 | Boyde | |
| 7,182,085 B1 | 2/2007 | Larsen et al. | |
| 7,264,604 B1 | 9/2007 | Schuren et al. | |
| 7,652,190 B2 * | 1/2010 | Johnson | 602/48 |
| 7,727,173 B2 | 6/2010 | Rooney | |
| 7,959,624 B2 * | 6/2011 | Riesinger | 604/543 |
| 7,976,519 B2 * | 7/2011 | Bubb et al. | 604/289 |
| 2003/0036716 A1 * | 2/2003 | Knutson et al. | 602/43 |
| 2006/0189909 A1 | 8/2006 | Hurley et al. | |
| 2007/0185428 A1 * | 8/2007 | Harder | 602/75 |
| 2008/0167631 A1 * | 7/2008 | Greer | A61M 1/0088 604/290 |
| 2009/0234259 A1 | 9/2009 | Hardman et al. | |
| 2009/0234260 A1 | 9/2009 | Coward et al. | |
| 2009/0234264 A1 * | 9/2009 | Randolph | 602/42 |
| 2010/0121286 A1 | 5/2010 | Locke et al. | |
| 2010/0145246 A1 | 6/2010 | Cadena | |
| 2010/0210983 A1 | 8/2010 | Baker et al. | |
| 2011/0054409 A1 * | 3/2011 | Nishtala | 604/179 |
| 2011/0152796 A1 * | 6/2011 | Kazala et al. | 604/290 |

* cited by examiner

*Primary Examiner* — Ophelia A Hawthorne
(74) *Attorney, Agent, or Firm* — Eric Karich; Karich & Associates

(57) ABSTRACT

A dressing device has a device body, a bore extending into an inner surface of the device body, and a biasing element positioned within the bore for biasing the dressing element against the ulcer. The device body functions to offload pressure from an ulcer of a patient. The biasing element functions to support a dressing element against the ulcer to medicate the ulcer, and to prevent the formation of proud flesh.

11 Claims, 2 Drawing Sheets

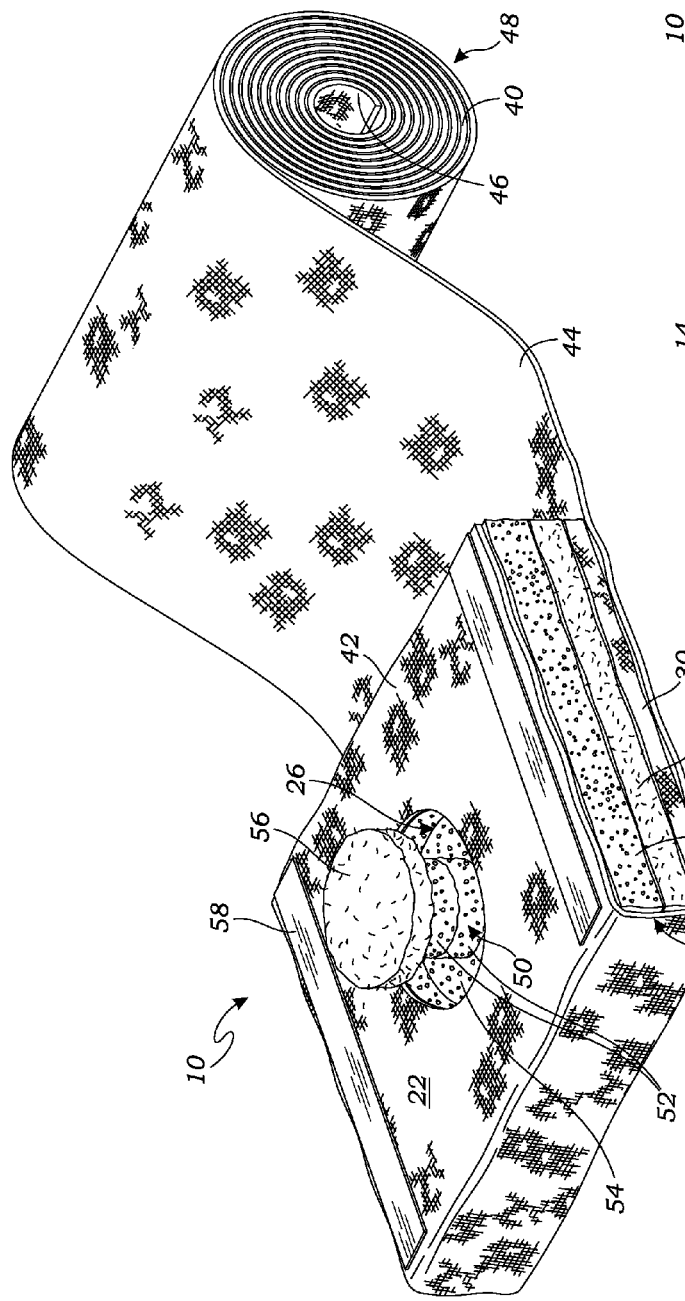
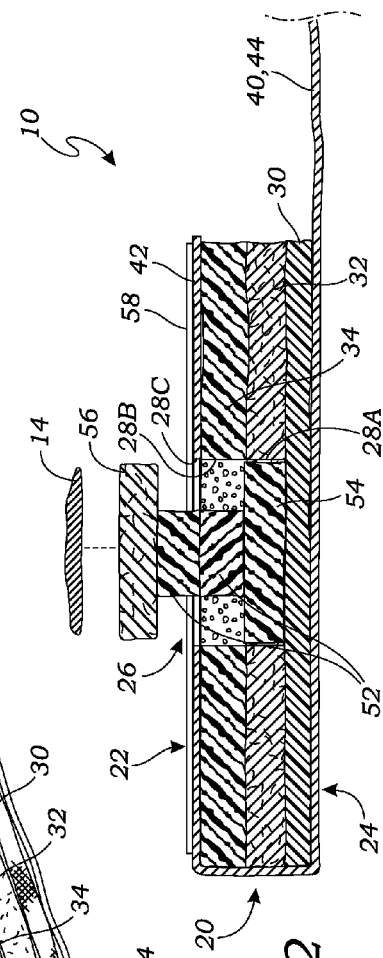
Fig. 1
Fig. 2

DRESSING DEVICE FOR OFFLOADING AND TREATING AN ULCER

BACKGROUND OF THE INVENTION

1. Field of the Invention

This invention relates generally to dressings, and more particularly to a dressing device for offloading and treating an ulcer.

2. Description of Related Art

Ulcers, especially on the foot, can be particularly difficult to heal, and can become life threatening if not handled quickly and effectively. Important issues that must be addressed in treating a foot ulcer include offloading pressure from the ulcer, infection control, and drainage. Offloading requires that excess pressure be removed from the ulcer, so that proper healing can take place. Infection control typically consists of maintaining a medicated dressing in proper contact with the ulcer. Managing drainage requires that the ulcer be kept dry, but not so dry that healing is hindered.

The prior art teaches a wide range of products that are used to offload an ulcer. A wheelchair may be required in some cases, to keep the patient completely off of the ulcer; however, this is undesirable for obvious reasons, and it is desirable for the patient to maintain mobility during treatment. Total contact casts can be effective, but they are difficult and time consuming to apply. Removable cast-walkers can be effective, but they face issues with patient compliance, since they can be easily removed by the patient. The prior art also teaches a wide variety of shoes and inserts that can be used to offload an ulcer.

Various patents teach wound treatment systems that attempt to provide the necessary treatment to ulcers. Hurley, U.S. 2006/0189909, for example, teaches a load relieving wound dressing that includes a three layer construction that includes a cushioning layer, an offloading layer, and a conforming layer. This construction further includes a load relieving aperture that offloads pressure from the ulcer.

Cavanagh, U.S. Pat. No. 6,720,470, teaches a wound treatment system that includes a donut shaped dressing that includes an aperture for offloading the ulcer. This bandage also teaches the inclusion of a "manifold" in the dressing aperture, the manifold being adapted to contact the ulcer.

Hardman, U.S. 2009/0234259, teaches a rigid shoe-type treatment device that includes removable portions that enable the creation of a depression adjacent the ulcer for relieving the pressure on an ulcer, and a foam manifold positioned in the depression for contacting the ulcer. These references are hereby incorporated by reference in full.

The prior art teaches various forms of devices that include apertures or depressions for offloading pressure from an ulcer. However, the prior art does not teach a dressing device that offloads pressure from the ulcer, provides for drainage from the ulcer, and also includes a resilient element for biasing a dressing against the ulcer. The present invention fulfills these needs and provides further related advantages as described in the following summary.

SUMMARY OF THE INVENTION

The present invention teaches certain benefits in construction and use which give rise to the objectives described below.

The present invention provides a dressing device for offloading pressure from an ulcer of a patient, and for supporting a dressing element against the ulcer. The dressing device includes a device body having an inner surface and an outer surface, a bore extending into the inner surface of the device body, and a biasing element positioned within the bore for biasing the dressing element against the ulcer.

A primary objective of the present invention is to provide a dressing device having advantages not taught by the prior art.

Another objective is to provide a dressing device that offloads pressure from an ulcer, such as a diabetic ulcer, so that the ulcer can heal.

Another objective is to provide a dressing device that includes a biasing element for biasing a dressing against the ulcer, to support proper ulcer healing, to keep medications on the dressing in contact with the ulcer, and to prevent the formation of proud flesh.

Another objective is to provide a dressing device that supports proper ulcer drainage.

Another objective is to provide a dressing device that includes an integral bandage that can be wrapped around the dressing device and the patient to enable the dressing device to be quickly and easily applied and removed.

A further objective is to provide a dressing device this is inexpensive and comfortable for the patient to wear.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings:

FIG. 1 is a perspective view of a dressing device according to one embodiment of the present invention;

FIG. 2 is a sectional view thereof taken along line 2-2 in FIG. 1; and

DETAILED DESCRIPTION OF THE INVENTION

Figure 3:
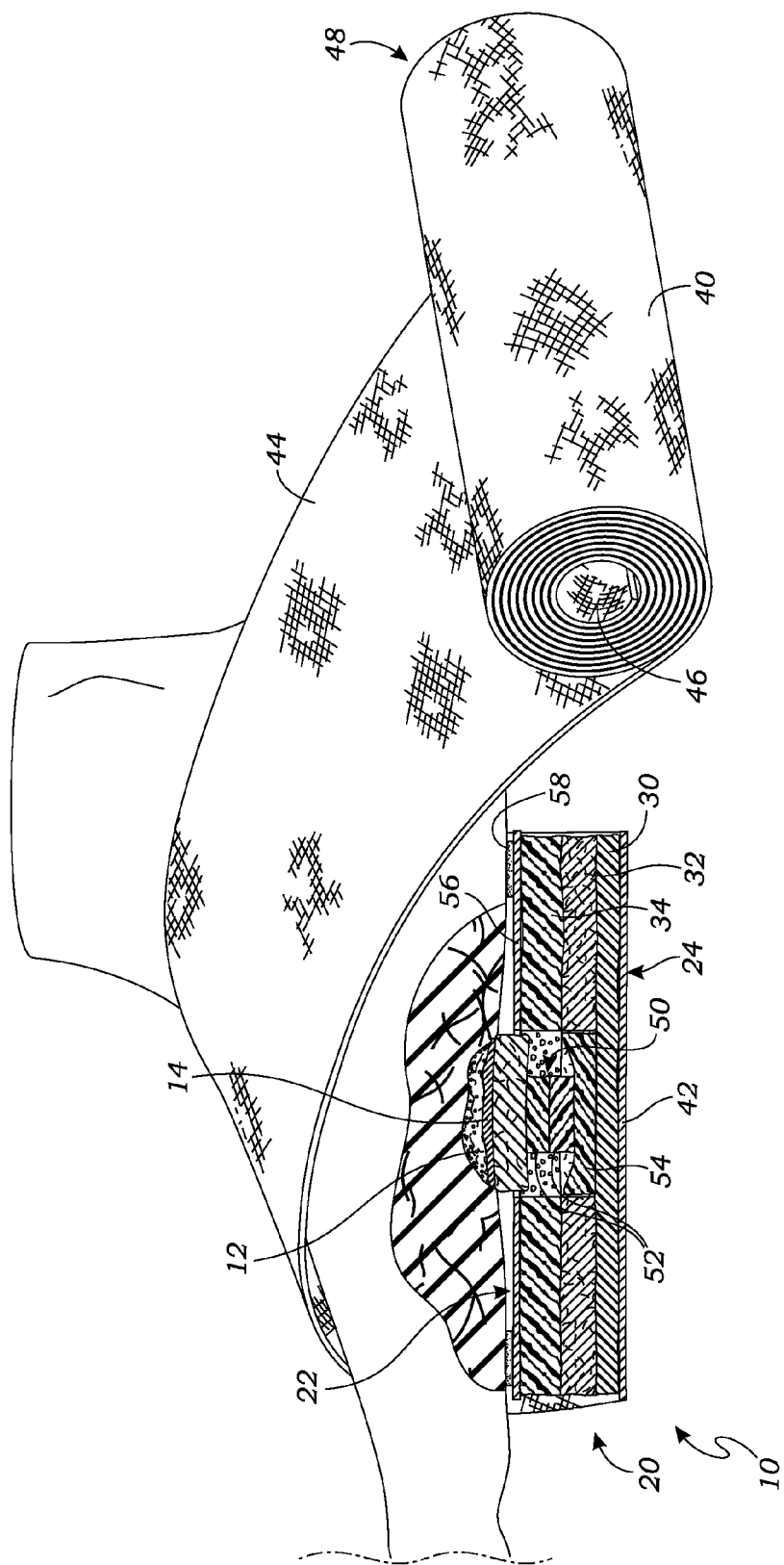
FIG. 3 is a perspective view of the dressing device being applied to an ulcer.

The above-described drawing figures illustrate the invention, a dressing device 10 for offloading pressure from an ulcer 12 of a patient, and for supporting a dressing element 14 against the ulcer 12.

FIG. 1 is a perspective view of the dressing device 10 according to one embodiment of the present invention. FIG. 2 is a sectional view thereof taken along line 2-2 in FIG. 1. As shown in FIGS. 1-2, the dressing device 10 comprises a device body 20 having an inner surface 22 and an outer surface 24, a bore 26 extending into the inner surface 22 of the device body 20, and a biasing element 50 positioned within the bore 26 for biasing the dressing element 14 against the ulcer 12. The dressing element 14 may include medications to treat the ulcer 12, the term medications being defined to include any form of medicines, disinfectants, salves, ointments, drugs, pharmaceuticals, and/or other applications that are helpful in treating and/or healing the ulcer 12.

In the embodiment of FIGS. 1 and 2, the device body 20 comprises a base layer 30 that forms the outer surface 24 of the device body 20, an absorbent layer 32 supported by the base layer 30, and a cushioning foam layer 34 supported by the absorbent layer 32, the cushioning foam layer 34 forming the inner surface 22 of the device body 20.

The base layer 30 provides a platform that supports and encompasses the remainder of the dressing device 10, and it preferably is soft enough to avoid abrading the user while it is worn. The base layer 30 may include a closed cell foam, such as a cross-linked polyethylene foam, preferably a foam that does not include residual chemicals that might be harmful to the patient's skin. A foam blown with nitrogen may be used to avoid many such chemicals. In one embodiment, a closed cell cross-linked polyethylene foam such as PLASTAZOTE® (a registered trademark of Zotefoams, PLC) may be used. In alternative embodiments, other suitable materials known in the art may be utilized.

The absorbent layer 32 functions to absorb and contain drainage from the ulcer 12 without desiccating the ulcer 12, and also functions to provide enough thickness to the device body 20 to enable the function of the device body 20 to offload the ulcer 12, as described in greater detail below. In one embodiment, the absorbent layer 32 includes a non-woven cloth, such as felt. In alternative embodiments, other suitable materials known in the art may be utilized.

The cushioning foam layer 34 foam functions to contour to the patient's body and provide a cushion so that the patient is comfortable and the area around the ulcer 12 is not traumatized or irritated. In one embodiment, the cushioning foam layer 34 may be a memory foam, such as an open cell temperature-sensitive "temper" foam. In alternative embodiments, other suitable materials known in the art may be utilized.

In the embodiment of FIGS. 1 and 2, the dressing device 10 further includes a bandage 40 for attaching the dressing device 10 to the patient. The bandage 40 may include a proximal end 42 and a main body 44 extending to a distal end 46, and may be initially formed into a roll 48 that may be easily shipped, stored, and maintained in a sterile condition. In this embodiment, the proximal end 42 may be adhered to the inner surface 22 of the device body 20 and wrapped around the outer surface 24 of the device body 20, maintaining the bandage 40 ready for use. Once the dressing device 10 has been placed over the ulcer 12, as discussed below, the main body 44 of the bandage 40 may be wrapped around the patient and the dressing device 10 to bind the dressing device 10 against the ulcer 12. The bandage 40 may be, for example, a gauze bandage 40, although other products and materials known in the art may also be used.

In the embodiment of FIGS. 1 and 2, the bore 26 is formed by a first bore aperture 28B through the cushioning foam layer 34, a second bore aperture 28A through the absorbent layer 32, and a third bore aperture 28C through the bandage 40. The base layer 30 provides support for the biasing element 50 positioned within the bore 26. In this embodiment, the biasing element 50 comprises a biasing base 54 that has a diameter equal to a diameter of the bore 26, and a resilient biasing portion 52 supported upon the biasing base 54.

In this embodiment, the biasing base 54 has a diameter that is generally equal to the second bore aperture 28B through the absorbent layer 32, so that the biasing base 54 fits within and frictionally engages the absorbent layer 32. The biasing base 54 may be formed of memory foam, or other suitable material, and forms a support for the resilient biasing portion 52.

The resilient biasing portion 52 has, at least in part, a diameter that is less than the diameter of the bore 26, and may include at least one layer (in this case two layers) of open cell memory foam. Since the diameter of the resilient biasing portion 52 is smaller than the diameter of the bore 26, this enables the resilient biasing portion 52 to move with respect to the device body 20.

Finally, a dressing support platform 56 is supported upon the resilient biasing portion 52 for supporting the dressing element 14 against the ulcer 12. The dressing support platform 56 is preferably constructed of an absorbent material that functions to absorb drainage from the wound, as discussed above. In one embodiment, the dressing support platform 56 is constructed of non-woven cloth, such as felt, although other suitable materials known in the art may be used. The dressing support platform 56 preferable has a diameter of approximately equal to the bore 26, so that the bore 26 is covered by the dressing support platform 56, although this is defined to include a significant variation in actual diameter measurements, because the specific diameter is not critical, and a wide tolerance is possible.

While one embodiment of the biasing element 50 is described and illustrated, those skilled in the art may devise alternative constructions that function to maintain the dressing element 14 against the ulcer 12 as described herein, and such alternatives should be considered within the scope of the present invention.

FIG. 3 is a perspective view of the dressing device 10 being applied to an ulcer 12. As illustrated in FIGS. 1-3, the dressing device 10 is applied to the patient so that the dressing element 14 contacts the ulcer 12, the dressing support platform 56 supports the dressing element 14 against the ulcer 12, and the bore 26 is positioned over the ulcer 12 so that the ulcer 12 is properly offloaded. Adhesive strips 58 may be positioned on the inside surface of the device body 20 to secure the device body 20 in place once it has been properly positioned.

In this position, the resilient biasing portion 52 provides a bias against the ulcer 12 sufficient to maintain proper contact between the dressing element 14 and the ulcer 12, and to prevent the formation of proud flesh, but not enough pressure to harm the ulcer 12. Weight applied to the dressing device 10, such as the user walking on an ulcerated foot, is offloaded by the device body 20.

Once the dressing element 14 and the device body 20 have been properly positioned, the bandage 40 is wrapped around the patient and the device body 20 multiple times until the device body 20 is securely fastened in place.

As used in this application, the words "a," "an," and "one" are defined to include one or more of the referenced item unless specifically stated otherwise. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application.

What is claimed is:

1. A dressing device for offloading pressure from an ulcer of a patient, and for supporting a dressing element against the ulcer, the dressing device comprising:
   a device body having an inner surface and an outer surface, wherein the device body comprises:
      a base layer that forms the outer surface of the device body, the base layer being formed of a closed cell foam;
      an absorbent layer supported by the base layer, the absorbent layer being formed of a nonwoven fabric; and
      a cushioning foam layer supported by the absorbent layer, the cushioning foam layer forming the inner surface of the device body, and being formed by an open cell foam;
   a bandage;
   a bore extending into the inner surface of the device body, the bore having a diameter, the bore being formed by a first bore aperture through the cushioning foam layer and a second bore aperture through the absorbent layer, and a third bore aperture through the bandage;

a biasing element positioned within the bore and bonded to the device body, at least a portion of the biasing element having a diameter that is smaller than the diameter of the bore, so that the biasing element is substantially separated from the device body; and a dressing support platform comprising an absorbent material bonded to the biasing element and operably positioned over the bore to support the dressing element against the ulcer.

2. The dressing device of claim 1, wherein the biasing element comprises:

a biasing base that has a diameter equal to a diameter of the bore; and a resilient biasing portion supported upon the biasing base, the resilient biasing portion having a diameter that is less than the diameter of the bore, the resilient biasing portion being bonded to the dressing support platform.

3. The dressing device of claim 2, wherein the dressing support platform is constructed of non-woven cloth, and having a diameter approximately equal to the diameter of the bore.

4. The dressing device of claim 2, wherein the dressing support platform is constructed of felt.

5. The dressing device of claim 2, wherein the resilient biasing portion includes at least one layer of open cell memory foam.

6. The dressing device of claim 1, wherein the bandage is a gauze bandage.

7. A dressing device for offloading pressure from an ulcer of a patient, and for supporting a dressing element against the ulcer, the dressing device comprising:

a device body having an inner surface and an outer surface, wherein the device body comprises:

a base layer that forms the outer surface of the device body, the base layer being formed of a closed cell foam;

an absorbent layer supported by the base layer, the absorbent layer being formed of a nonwoven fabric; and a cushioning foam layer supported by the absorbent layer, the cushioning foam layer forming the inner surface of the device body, and being formed by an open cell foam;

a bandage having a proximal end and a main body extending to a distal end, the proximal end being attached to the device body such that the main body may be wrapped around the patient and the dressing device to bind the dressing device against the ulcer;

a bore extending into the inner surface of the device body, the bore having a diameter, the bore being formed by a first bore aperture through the cushioning foam layer and a second bore aperture through the absorbent layer, and a third bore aperture through the bandage;

a biasing element positioned within the bore for biasing the dressing element against the ulcer, the biasing element comprising a resilient biasing portion having a diameter that is less than the diameter of the bore.

8. The dressing device of claim 7, further comprising a dressing support platform mounted on the biasing element.

9. The dressing device of claim 8, further comprising a dressing element operably supported by the dressing support platform.

10. The dressing device of claim 9, wherein the dressing element is medicated.

11. A dressing device for offloading pressure from an ulcer of a patient, the dressing device comprising:

a device body having an inner surface and an outer surface, the device body comprising:

a base layer that forms the outer surface of the device body;

an absorbent layer supported by the base layer; and a cushioning foam layer supported by the absorbent layer, the cushioning foam layer forming the inner surface of the device body;

a bore extending into the inner surface of the device body, the bore being formed by a first bore aperture through the cushioning foam layer and a second bore aperture through the absorbent layer;

a biasing element positioned within the bore for biasing the dressing element against the ulcer, the biasing element comprising a biasing base that has a diameter equal to a diameter of the bore, and a resilient biasing portion supported upon the biasing base, the resilient biasing portion having a diameter that is less than the diameter of the bore;

a dressing element adapted for contacting the ulcer;

a dressing support platform supported upon the resilient biasing portion for supporting the dressing element against the ulcer; and a bandage having a proximal end and a main body extending to a distal end, the proximal end being attached to the device body such that the main body may be wrapped around the patient and the dressing device to bind the dressing device against the ulcer, the bandage having a third bore aperture.

* * * * *